United States Patent
Kuo et al.

(10) Patent No.: US 10,937,521 B2
(45) Date of Patent: Mar. 2, 2021

(54) CLASSIFICATION SYSTEM AND CLASSIFICATION METHOD OF AUTOANTIBODY IMMUNOFLUORESCENCE IMAGE

(71) Applicant: CHANG GUNG MEMORIAL HOSPITAL, LINKOU, Taoyuan (TW)

(72) Inventors: Chang-Fu Kuo, Taoyuan (TW); Chi-Hung Lin, Taoyuan (TW); Yi-Ling Chen, Taoyuan (TW); Meng-Jiun Chiou, Taoyuan (TW)

(73) Assignee: CHANG GUNG MEMORIAL HOSPITAL, LINKOU, Taoyuan (TW)

( * ) Notice: Subject to any disclaimer, the term of this patent is extended or adjusted under 35 U.S.C. 154(b) by 42 days.

(21) Appl. No.: 16/397,379

(22) Filed: Apr. 29, 2019

(65) Prior Publication Data

US 2019/0371425 A1 Dec. 5, 2019

(30) Foreign Application Priority Data

May 29, 2018 (TW) .................................. 107118280

(51) Int. Cl.
*G06T 7/00* (2017.01)
*G16B 5/00* (2019.01)
*G06K 9/00* (2006.01)

(52) U.S. Cl.
CPC ............. *G16B 5/00* (2019.02); *G06K 9/0014* (2013.01); *G06K 9/00147* (2013.01); *G06T 7/0012* (2013.01); *G06T 2207/10064* (2013.01); *G06T 2207/20084* (2013.01); *G06T 2207/30024* (2013.01)

(58) Field of Classification Search
CPC ............. G06K 9/0014; G06K 9/00147; G06K 9/6273; G06T 2207/10064; G06T 2207/20084; G06T 2207/30024; G06T 7/0012; G16B 5/00
See application file for complete search history.

(56) References Cited

U.S. PATENT DOCUMENTS

| | | | | |
|---|---|---|---|---|
| 6,007,996 A | * | 12/1999 | McNamara | C12Q 1/6841 382/129 |
| 6,463,438 B1 | * | 10/2002 | Veltri | G06K 9/0014 706/15 |
| 7,761,240 B2 | * | 7/2010 | Saidi | G06T 7/0012 702/19 |
| 2008/0166035 A1 | * | 7/2008 | Qian | G06T 7/0012 382/133 |

(Continued)

*Primary Examiner* — Ian L Lemieux
(74) *Attorney, Agent, or Firm* — WPAT, PC

(57) ABSTRACT

A classification system and a classification method of the autoantibody immunofluorescence image are disclosed. The system includes an input device, a processor and an output device. The plurality of cell immunofluorescence images and the corresponded extractable nuclear antigen results are input through the input device. The processor conducts a plurality of convolution neural network calculation and output the classification based on the extractable nuclear antigen results, so as to obtain an extractable nuclear antigen classification model. When the autoantibody immunofluorescence image is input by the input device, the corresponded classification of the extractable nuclear antigen can be predicted. The classification result is output through the output device.

18 Claims, 7 Drawing Sheets

(56) References Cited

U.S. PATENT DOCUMENTS

| | | | | |
|---|---|---|---|---|
| 2010/0002929 A1* | 1/2010 | Sammak | ............ | G06K 9/00127 |
| | | | | 382/133 |
| 2010/0177950 A1* | 7/2010 | Donovan | ............... | G16H 50/30 |
| | | | | 382/133 |
| 2013/0024177 A1* | 1/2013 | Nolan | .................... | G16H 50/50 |
| | | | | 703/11 |
| 2013/0218474 A1* | 8/2013 | Longo | .............. | G01N 33/56972 |
| | | | | 702/19 |
| 2019/0340473 A1* | 11/2019 | Kuo | ......................... | G06T 5/50 |

* cited by examiner

CLASSIFICATION SYSTEM AND CLASSIFICATION METHOD OF AUTOANTIBODY IMMUNOFLUORESCENCE IMAGE

CROSS-REFERENCE TO RELATED APPLICATION

This application claims priority of Taiwan patent application No. 107118280, filed on May 29, 2018, the content of which is incorporated herein in its entirety by reference.

BACKGROUND OF THE INVENTION

1. Field of the Invention

The present invention relates to a classification system and a classification method of immunofluorescence images of autoantibodies, particularly to a classification system and a classification method for analyzing original cell immunofluorescence images using an operation of convolutional neural networks (CNN), and predicting various types of extractable nuclear antigens in the immunofluorescence images.

2. The Prior Art

Antinuclear antibodies (ANA) can be regarded as a group of autoantibodies that use various nuclear-related components in human cells as targets. These autoantibodies are present in a variety of immune diseases, such as rheumatoid arthritis, lupus erythematosus, scleroderma, xerosis, dermatomyositis, etc., and play a very important role in the diagnosis of pediatric rheumatic diseases. At present, the standard screening method for screening autoantibodies is to test by indirect immunofluorescence (IIF). If the result is greater than or equal to 1:80 after dilution, the readout can be recognized to be a meaningful positive result, that is, associated with a variety of autoimmune diseases. Then, in conjunction with blood examinations, different types of extractable nuclear antigen (ENA) examinations can be performed to further find out the correspondence with immune diseases as a recognition as to whether or not they are classified as specific immune diseases. However, the interpretation of current fluorescent images is mostly conducted by manual interpretation, which causes a burden on labor demands. There are also many types of examinations for extractable nuclear antigens. When deciding on the examination items, it is necessary to consider how to select the corresponding extractable nuclear antigen examination categories.

In this regard, the use of machine learning technology to deal with the interpretation of immunofluorescent images seems to be a solution to solve the problems about labor costs of the manual interpretation and interpretation consistency. However, in the prior art, it is necessary to pre-process the original cell immunofluorescence images before conducting machine interpretation, such as defined cutting of the cell range boundary, pixel blurring processing, etc., in order to obtain a more effective interpretation result. However, the pre-processed procedure increases the step of interpretation, reduces the interpretation efficiency of the antinuclear antibody results, and does not directly link to the blood examination results of extractable nuclear antigens. Therefore, the current methods for examining and recognizing antinuclear antibodies are still unable to directly use the machine learning method to complete the interpretation of immunofluorescence images and predict the types of extractable nuclear antigens in a simplified and accurate manner.

In view of this, how to establish a machine learning model, which can directly read the original cell immunofluorescence images, capture the characteristics, learn by inputting the actual detection results of extractable nuclear antigens, and establish a corresponding anti-nuclear antibody classification model improves the efficiency and accuracy of interpretation results. Therefore, the inventors of the present invention have conceived and designed a classification system and a classification method of immunofluorescence images of autoantibodies, and the drawbacks have been improved in view of the lack of the prior art, thereby enhancing the industrial use and utilization.

SUMMARY OF THE INVENTION

In view of the above-mentioned problems of the prior art, the objective of the present invention is to provide a classification system and a classification method of immunofluorescence images of autoantibodies, so as to solve the problems that the automatic interpretation accuracy is too low and the antinuclear antibody classification cannot be predicted in the prior art.

A primary objective of the present invention is to provide a classification system of immunofluorescence images of autoantibodies, comprising: an input device, a processor, and an output device. The input device is configured to input a plurality of cell immunofluorescence images and an extractable nuclear antigen result corresponding to the plurality of cell immunofluorescence images. The processor is connected to the input device, wherein the processor converts the plurality of cell immunofluorescence images into a plurality of three primary color layers, respectively, and conducts an operation of a plurality of convolutional neural networks, wherein each of the plurality of convolutional neural networks comprises a convolution layer, a pooling layer and an inception layer for capturing a plurality of convolution features after the operation, wherein the plurality of convolution features are used as input of next order of convolutional neural networks, wherein the plurality of convolution features are fully connected with the extractable nuclear antigen result, wherein the processor obtains an extractable nuclear antigen classification model via proportions of the plurality of cell immunofluorescence images to a plurality of extractable nuclear antigens. The output device is connected to the processor, wherein the output device outputs an extractable nuclear antigen classification result generated by the processor; wherein the extractable nuclear antigen classification result is the plurality of extractable nuclear antigens predicted by the processor corresponding to a cell immunofluorescence image under test input by the input device according to the extractable nuclear antigen classification model.

Preferably, the input device inputs a correspondence table of the plurality of extractable nuclear antigens corresponding to a plurality of disease types, the processor establishes a disease classification model by the plurality of cell immunofluorescence images belong to the plurality of disease types, and the output device outputs a disease classification result generated by the processor. The disease classification result is the plurality of disease types predicted by the processor corresponding to the cell immunofluorescence image under test according to the disease classification model.

Preferably, the plurality of extractable nuclear antigens respectively correspond to at least one of the plurality of disease types.

Preferably, the convolution layer comprises a trigger function, and the trigger function comprises a Sigmoid function, a Tan h function, a ReLU function, a PReLU function, an ArcTan function, an ELU function, a SoftPlus function, a Sinusoid function, a Sin c function, a Bent identity function, or a Gaussian function.

Preferably, the pooling layer comprises a max-pooling operation or a mean pool operation.

Preferably, the inception layer comprises a convolution operation and a max-pooling operation for different sizes of templates in a same layer of operation, and then data are cascaded.

Preferably, each of the plurality of extractable nuclear antigens comprises dsDNA, ssDNA, RNA, Histone, U14-RNP, Sm, SS-A, SS-B, U3-nRNP/Fibrillarin, RNA polymerase 1, RNA helicase A, PM-Scl, centromeres, Topoisomerase 1, PCNA-like, Ku, Mi-1, Mi-2, Nucleosome, DFS-70, TIF1-gamma, hnRNP, RNA polymerase III, Sp100, Sp140, p80-coilin, NOR-90, gp210, lamin A, b, c and lamin B receptor, F-actin, tropomyosin, vimentin, vinculin, GWB proteins, PL-7, PL-12, ribosomal P, SRP, JO-1, AMA-M2, giantin/macrogolgin, golgin-95/GM130, pericentrin, ninein, Cep250 and Cep110, HsEG5, NUMA, and CENP-F like.

Preferably, the plurality of cell immunofluorescence images are subjected to an operation of 10-layer convolutional neural networks to capture the plurality of convolution features.

Preferably, the convolution layer in each of the plurality of convolutional neural networks has a convolution kernel of a predetermined pixel size.

Another objective of the present invention is to provide a classification method of immunofluorescence images of autoantibodies, comprising the following steps: inputting a plurality of cell immunofluorescence images and an extractable nuclear antigen result corresponding to the plurality of cell immunofluorescence images through an input device; converting the plurality of cell immunofluorescence images into a plurality of three primary color layers, respectively, and conducting an operation of a plurality of convolutional neural networks via a processor, wherein each of the plurality of convolutional neural networks comprises a convolution layer, a pooling layer and an inception layer for capturing a plurality of convolution features after the operation, followed by using the plurality of convolution features as input of next order of convolutional neural networks; conducting a classification process via the processor, fully connecting the plurality of convolution features with the extractable nuclear antigen result, and obtaining an extractable nuclear antigen classification model via proportions of the plurality of cell immunofluorescence images to a plurality of extractable nuclear antigens; inputting a cell immunofluorescence image under test through the input device, and predicting an extractable nuclear antigen classification result in the cell immunofluorescence image under test according to the extractable nuclear antigen classification model by the processor; and outputting the extractable nuclear antigen classification result through an output device.

Preferably, the classification method further comprises the following steps: inputting a correspondence table of the plurality of extractable nuclear antigens corresponding to a plurality of disease types through the input device, and establishing a disease classification model by the plurality of cell immunofluorescence images belong to the plurality of disease types through the processor; predicting a disease classification result of the plurality of disease types corresponding to the cell immunofluorescence image under test according to the disease classification model via the processor; and outputting the disease classification result through the output device.

Preferably, the plurality of extractable nuclear antigens respectively correspond to at least one of the plurality of disease types.

Preferably, the convolution layer comprises a trigger function, and the trigger function comprises a Sigmoid function, a Tan h function, a ReLU function, a PReLU function, an ArcTan function, an ELU function, a SoftPlus function, a Sinusoid function, a Sin c function, a Bent identity function, or a Gaussian function.

Preferably, the pooling layer comprises a max-pooling operation or a mean pool operation.

Preferably, the inception layer comprises a convolution operation and a max-pooling operation for different sizes of templates in a same layer of operation, and then data are cascaded.

Preferably, each of the plurality of extractable nuclear antigens comprises dsDNA, ssDNA, RNA, Histone, U14-RNP, Sm, SS-A, SS-B, U3-nRNP/Fibrillarin, RNA polymerase 1, RNA helicase A, PM-Scl, centromeres, Topoisomerase 1, PCNA-like, Ku, Mi-1, Mi-2, Nucleosome, DFS-70, TIF1-gamma, hnRNP, RNA polymerase III, Sp100, Sp140, p80-coilin, NOR-90, gp210, lamin A, b, c and lamin B receptor, F-actin, tropomyosin, vimentin, vinculin, GWB proteins, PL-7, PL-12, ribosomal P, SRP, JO-1, AMA-M2, giantin/macrogolgin, golgin-95/GM130, pericentrin, ninein, Cep250 and Cep110, HsEG5, NUMA, and CENP-F like.

Preferably, the plurality of cell immunofluorescence images inputted are subjected to an operation of 10-layer convolutional neural networks to capture the plurality of convolution features.

Preferably, the convolution layer in each of the plurality of convolutional neural networks has a convolution kernel of a predetermined pixel size.

According to the above, the classification system and the classification method of immunofluorescence images of autoantibodies according to the present invention may have one or more of the following advantages:

(1) The classification system and the classification method of immunofluorescence images of autoantibodies can directly analyze the original cell immunofluorescence image, and does not need to perform the pre-processed step on the immunofluorescence images, thereby effectively improving the interpretation efficiency. In addition, the classification system and the classification method of immunofluorescence images of autoantibodies can conduct a multi-layer operation of convolutional neural networks, obtaining the deep features of cell immunofluorescence images, making the interpretation results more accurate and improving the accuracy of recognition.

(2) The classification system and the classification method of immunofluorescence images of autoantibodies can establish a classification model of extractable nuclear antigens through machine learning, directly input cell immunofluorescence images to predict the type of extractable nuclear antigens, reduce the manual interpretation manner and the waste of excessive blood examination, and reduce the burden on inspectors and the cost of inspection.

(3) The classification system and the classification method of immunofluorescence images of autoantibodies can establish a disease classification model through machine learning, directly input cell immunofluorescence images to predict corresponding disease types, and improve the effectiveness of the classification results of various disease types.

BRIEF DESCRIPTION OF THE DRAWINGS

The following drawings form part of the present specification and are included here to further demonstrate some aspects of the present invention, which can be better understood by reference to one or more of these drawings, in combination with the detailed description of the embodiments presented herein.

DETAILED DESCRIPTION OF THE PREFERRED EMBODIMENT

In the following detailed description of the embodiments of the present invention, reference is made to the accompanying drawings, which are shown to illustrate the specific embodiments in which the present disclosure may be practiced. These embodiments are provided to enable those skilled in the art to practice the present disclosure. It is understood that other embodiments may be used and that changes can be made to the embodiments without departing from the scope of the present invention. The following description is therefore not to be considered as limiting the scope of the present invention.

Figure 1:
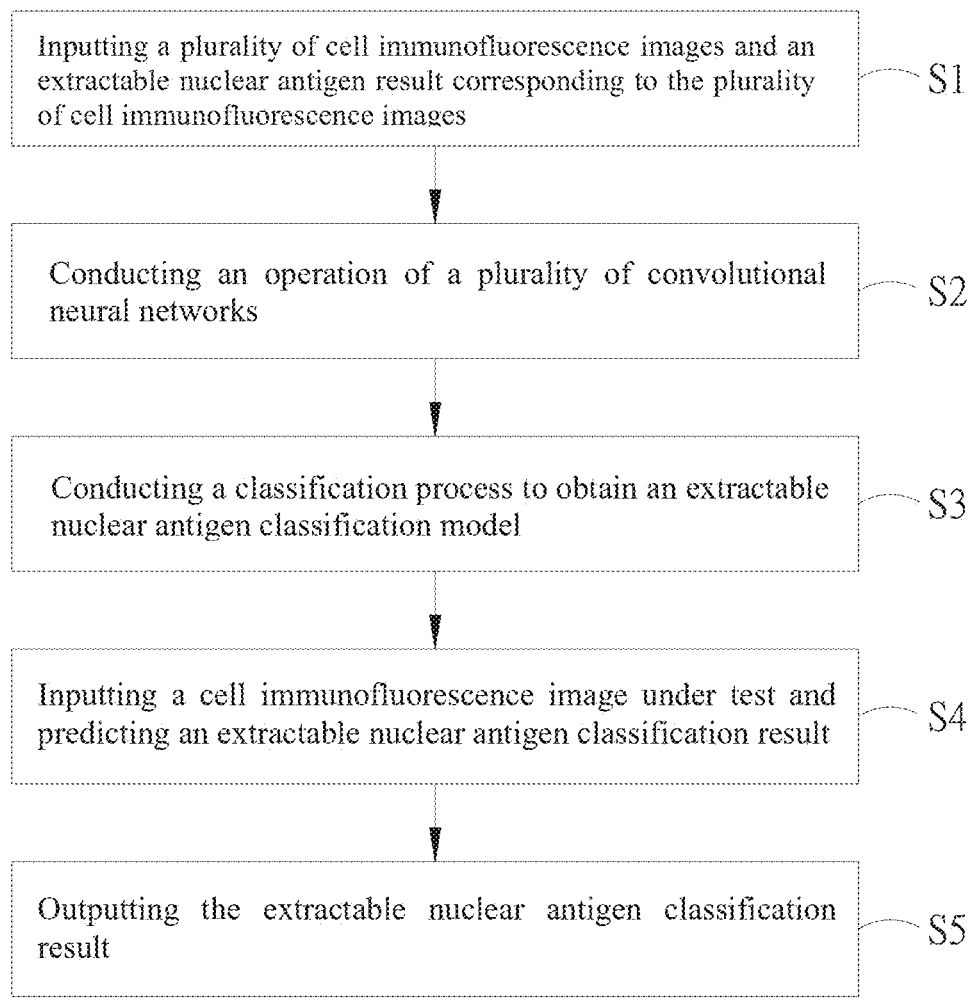
FIG. 1 is a flow chart showing a classification method of immunofluorescence images of autoantibodies according to an embodiment of the present invention.

Referring to FIG. 1, which is a flow chart showing a classification method of immunofluorescence images of autoantibodies according to an embodiment of the present invention. As shown in FIG. 1, the classification method of immunofluorescence images of autoantibodies comprises the following steps (S1 to S5):

Step S1: Inputting a plurality of cell immunofluorescence images and an extractable nuclear antigen result corresponding to the plurality of cell immunofluorescence images. The original immunofluorescence images produced by the immunofluorescence examination can be input into the classification system through an input device. The input device herein can be a shooting or capturing device, such as a camera, collecting the image of the examination, or transmitting and receiving the files of the cell immunofluorescence images using a computer interface or a network interface, and storing the files in a storage device, such as in the memory of a computer or the database of a server. At the same time, for these cell immunofluorescence images, data that has been tested for extractable nuclear antigens have been selected as training data for establishing a network model, that is, patients with cell immunofluorescence images have been performed with blood examinations for extractable nuclear antigens to confirm that the examination result of extractable nuclear antigens is positive or negative. The examination result of extractable nuclear antigens is input into the classification system as a marker of the cell immunofluorescence images, and the data are learned and trained to establish a classification model network.

Step S2: Conducting an operation of a plurality of convolutional neural networks. The cell immunofluorescence images input through the above steps may perform an operation step by executing a specific instruction through a processor, and the processor comprises a central processing unit of the computer, an image processor, a microprocessor, or a combination thereof. First, the cell immunofluorescence images are converted into layers of three primary colors (red, green, and blue) through the image conversion software. Compared with the prior art that is necessary to outline the cell appearance in the immunofluorescence images to analyze the differentiated cells, the three primary color layers of original immunofluorescence images are used as input data, and no additional image pre-processing is needed, thereby effectively improving the efficiency of analysis. The convolutional neural network comprises an operation of a convolution layer, a pooling layer and an inception layer. In this embodiment, the cell immunofluorescence images can be used to discover deeper features in the immunofluorescence images through multiple operations of convolutional neural network, so that the results of subsequent judgment or classification are more accurate. The operation criteria of the convolution layer, the pooling layer and the inception layer may be stored in the computer or server for analysis. The contents of each layer operation will be described separately below.

First, the convolution layer is a convolution kernel $k_{ij}^{l}$ of a predetermined size, convolving the feature data $x_i^{l-1}$ of the previous layer and adding the deviation value $b_j^{l}$, and the feature data $z_j^{l}$ after convolution, as shown in the following equation (1), is obtained. The convolution operation moves the convolution kernel through the sliding manner on the data, and calculates the inner product to obtain new features. The size of the convolution kernel can be designed in different sizes in operations of convolutional neural networks at different stages, so that the convolutions at different stages can be different.

$$z_j^{l} = \Sigma_i x_i^{l-1} \times k_{ij}^{l} + b_j^{i} \quad (1)$$

Then, the convolution layer comprises an activation layer, using the trigger function $f$ to convert the convolution features $z_j^{l}$ in the previous layer into $x_j^{l} = f(z_j^{l})$. Using the trigger function is to use a nonlinear function to avoid the linear combination of the input in the previous layer as the output in this layer. Common trigger functions comprise Sigmoid functions, Tan h functions, or ReLU functions. The Sigmoid function is shown in equation (2), and its output map is between 0 and 1. The Tan h function is shown in equation (3), which is centered at 0 and is distributed between −1 and 1. The ReLU function is shown in equation (4), and some of the neuron outputs are zero.

$$\text{sigmoid}(x) = \frac{1}{1+e^{-x}} \quad (2)$$

$$\tanh(x) = \frac{2}{1+e^{-2x}} - 1 \quad (3)$$

$$ReLU(x) = \max(0, x) \quad (4)$$

Among the above trigger functions, the Sigmoid function and the Tan h function have more and more layers in the hidden layer due to the development of deep learning. When the network model is used for back propagation, the gradient disappears easily, resulting in training problems. Therefore, in the present embodiment, the ReLU function is a preferable trigger function, and some of the neuron outputs are 0, making the network model sparser and reducing the phenomenon of over-fitting.

In addition to the above trigger function, the PReLU function, the ArcTan function, the ELU function, the SoftPlus function, the Sinusoid function, the Sin c function, the Bent identity function or the Gaussian function can also be used as the trigger function of the convolution layer. Among them, the PReLU function is shown in equation (5), which is an improvement of the ReLU function, and the learnable parameter a is added. The ArcTan function is shown in equation (6). The ELU function is similar to the PReLU function, adding a non-zero output to the negative input to prevent silent neurons from appearing and the reciprocal convergence is zero. The SoftPlus function returns any value greater than zero as shown in equation (7). The Sinusoid function, as shown in equation (8), forms a sinusoid with a range of −1 to 1. The sin c function is shown in equation (9), which defines a value of 1 when x is zero. The Bent identity function, as shown in equation (10), allows nonlinear behavior and can return values on either side of 1. The Gaussian function is shown in equation (11), and the range is between 0 and 1. The above activation function may be used as a trigger function of the activation layer in the embodiment of the present invention, but it is not limited thereto in the present invention.

$$PReLU(x) = \max(0, x) + a \times \min(0, x) \quad (5)$$

$$\arctan(x) = \frac{i}{2}\ln\left(\frac{i+x}{i-x}\right) \quad (6)$$

$$Softplus(x) = \ln(1 + e^x) \quad (7)$$

$$Sinusoid(x) = \sin(x) \quad (8)$$

$$Sinc(x) = \frac{\sin(x)}{x} \quad (9)$$

$$Bent\ Identity(x) = \frac{\sqrt{x^2+1}-1}{2} + x \quad (10)$$

$$Gaussian(x) = e^{-x^2} \quad (11)$$

Next, the pooling layer operation comprises a max-pooling mode or a mean pool mode. The max-pooling is to return the maximum value of each feature map, and the mean pool is to return the average value of each feature map, that is, the feature after the convolution layer and the activation layer, becoming a new feature after being pooled. The operation of the pooling layer calculates the maximum or average value in the kernel through the non-overlapping 1×n kernel, and reduces the data dimension of the immunofluorescent image data by n times. In this embodiment, the dimension of the feature data reduction by the pooling layer may be different in the operation of convolutional neural networks at different stages. In addition, in some of the operation of convolutional neural networks, the convolved feature data can be recombined to avoid the data dimension being too reduced to present the actual features of immunofluorescent images.

Figure 2:
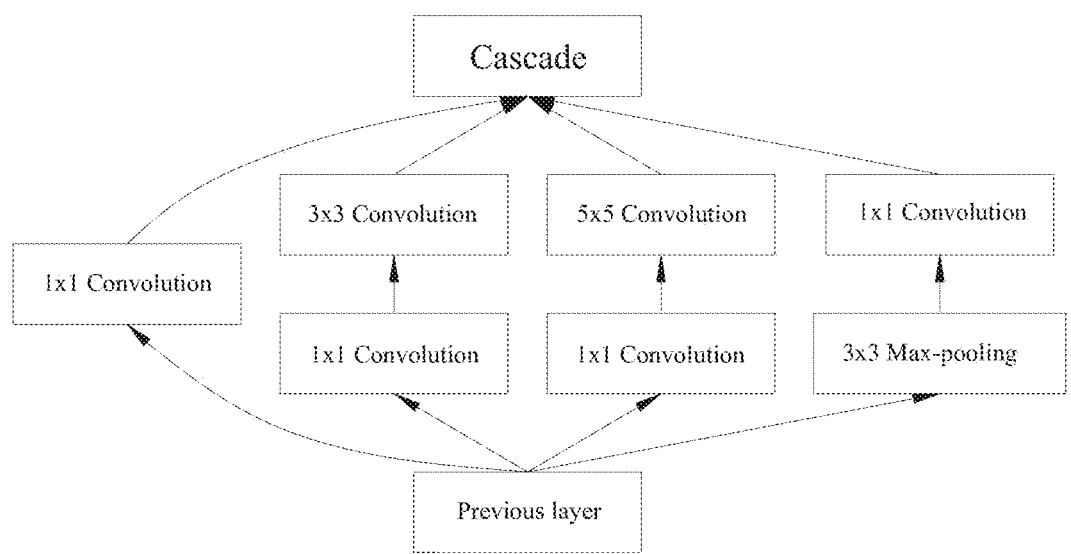
FIG. 2 is a schematic diagram of an inception layer of an embodiment of the present invention.

Finally, the inception layer operation uses a tree network architecture to increase the depth and width of the network model. Referring to FIG. 2, which is a schematic diagram of an inception layer of an embodiment of the present invention. As shown in FIG. 2, the feature data of the previous layer is concatenated with 1×1, 3×3, and 5×5 convolutions and 3×3 max-pooling, and finally cascaded, so that the inception layer can obtain different levels of features. However, in order to avoid excessive network computation, a 1×1 convolution is conducted before 3×3 and 5×5 convolution, reducing the number of input channels, increasing the depth of network analysis, but the amount of data computation is reduced, thereby improving the efficiency of the operation. In addition, a trigger function, such as the ReLU function, can be set after each convolution layer.

The above-mentioned feature extraction process of convolutional neural networks can perform multiple stages of convolutional neural network operations to the cell immunofluorescence image content, and obtain a plurality of convolution features. These convolution features can be used as the input data of another convolutional neural network, and the operations of the convolution layer, the pooling layer, and the inception layer are conducted again. By using multiple convolutional neural network operations, deeper hidden features are found.

Figure 3:
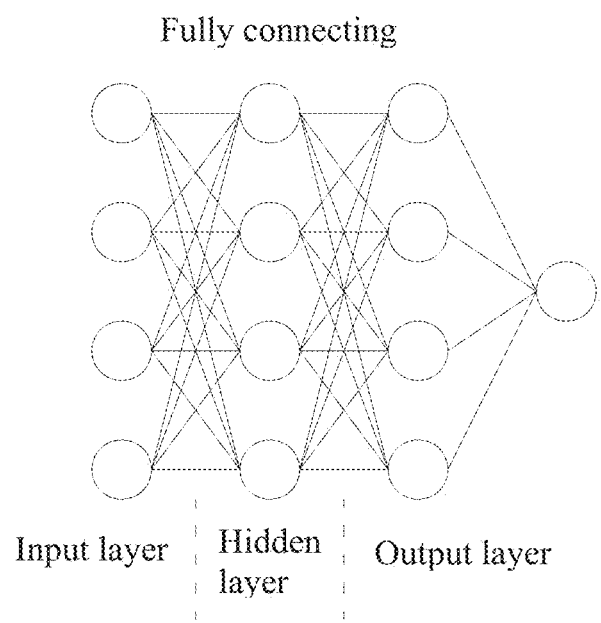
FIG. 3 is a schematic diagram of a multilayer sensing neural network according to an embodiment of the present invention.

Step S3: Conducting a classification process to establish an extractable nuclear antigen classification model. After the multi-layer convolutional neural network operation conducted by the processor for the above feature extraction, the obtained plurality of convolution features can be fully connected with the extractable nuclear antigen result, and the proportions of the cell immunofluorescence images to various types of extractable nuclear antigens and autoantibodies are recognized. Further, a network model of the relationship between cell immunofluorescence images and extractable nuclear antigens is established. That is, the extractable nuclear antigen classification model is established by the training data. Referring to FIG. 3, which is a schematic diagram of a multilayer sensing neural network according to an embodiment of the present invention. As shown in FIG. 3, combined with two layers of fully-connected manner, each neuron in the operation layer is connected to all neurons in the next layer for operation. However, the embodiment is not limited thereto. In another embodiment, a dropout manner may also be used. By setting the probability p, a plurality of neurons in each hidden layer are not added to the operation, for example, the set probability p may be 0.5. The reason for using the dropout manner is to avoid the over-fitting phenomenon that the prediction result of training data is good, but the result of the test data is not good. Using the dropout manner to set the probability, and randomly training each epoch to correct the weight, the neurons in the hidden layer have a certain probability to disappear, so that each neuron may not be updated when the weight is updated, thereby preventing over-fitting. For example, the dropout manner can be selected during training, and the fully connected manner can be selected during actual testing.

The output layer of the multilayer sensing neural network can be classified and predicted using the softmax function, as shown in the following equation (12), as a probability of expressing the prediction result.

$$\mathrm{softmax}(z)_j = \frac{e^{z_j}}{\sum_{k=1}^{K} e^{z_k}} \quad \text{for } j = 1, \ldots, K \quad (12)$$

Classification of various extractable nuclear antigens, mainly comprising dsDNA, ssDNA, RNA, Histone, U14-RNP, Sm, SS-A, SS-B, U3-nRNP/Fibrillarin, RNA polymerase 1, RNA helicase A, PM-Scl, Centromeres (cenp-A, cenp-B), Topoisomerase 1, PCNA-like, Ku, Mi-1, Mi-2, Nucleosome, DFS-70, TIF1-gamma, hnRNP, RNA polymerase III, Sp100, Sp140, p80-Coilin, NOR-90 (nucelolus organisator), gp210, lamin A, b, c and lamin B receptor, F-actin, tropomyosin, vimentin, vinculin, GWB proteins (GW182), PL-7, PL-12, ribosomal P, SRP, JO-1, AMA-M2, giantin/macrogolgin, golgin-95/GM130, pericentrin, ninein, Cep250 and Cep110, HsEG5 (MSA-2), NUMA (MSA-1), and CENP-F like.

Step S4: Inputting a cell immunofluorescence image under test, and predicting an extractable nuclear antigen classification result. After the established extractable nuclear antigen classification model and learning the training data, the cell immunofluorescence image under test is input via the input device, the multi-layer operation of convolutional networks is also conducted, and the extractable nuclear antigen classification result in the cell immunofluorescence image under test is predicted according to the extractable nuclear antigen classification model. Images of different characteristic types of cell immunofluorescence images may correspond to more than one type of extractable nuclear antigen.

Step S5: Outputting the extractable nuclear antigen classification result. After obtaining the extractable nuclear antigen classification result of cell immunofluorescence images through the above steps, the classification result may be stored in the storage device, and the recognition result is transmitted to the corresponding processing personnel through an output device. For example, the results are transmitted to the medical staff or medical examiner's computer, mobile phone, or tablet through wired or wireless network transmission, so that it can perform subsequent diagnosis or provide further instructions according to the classification results.

Figure 4:
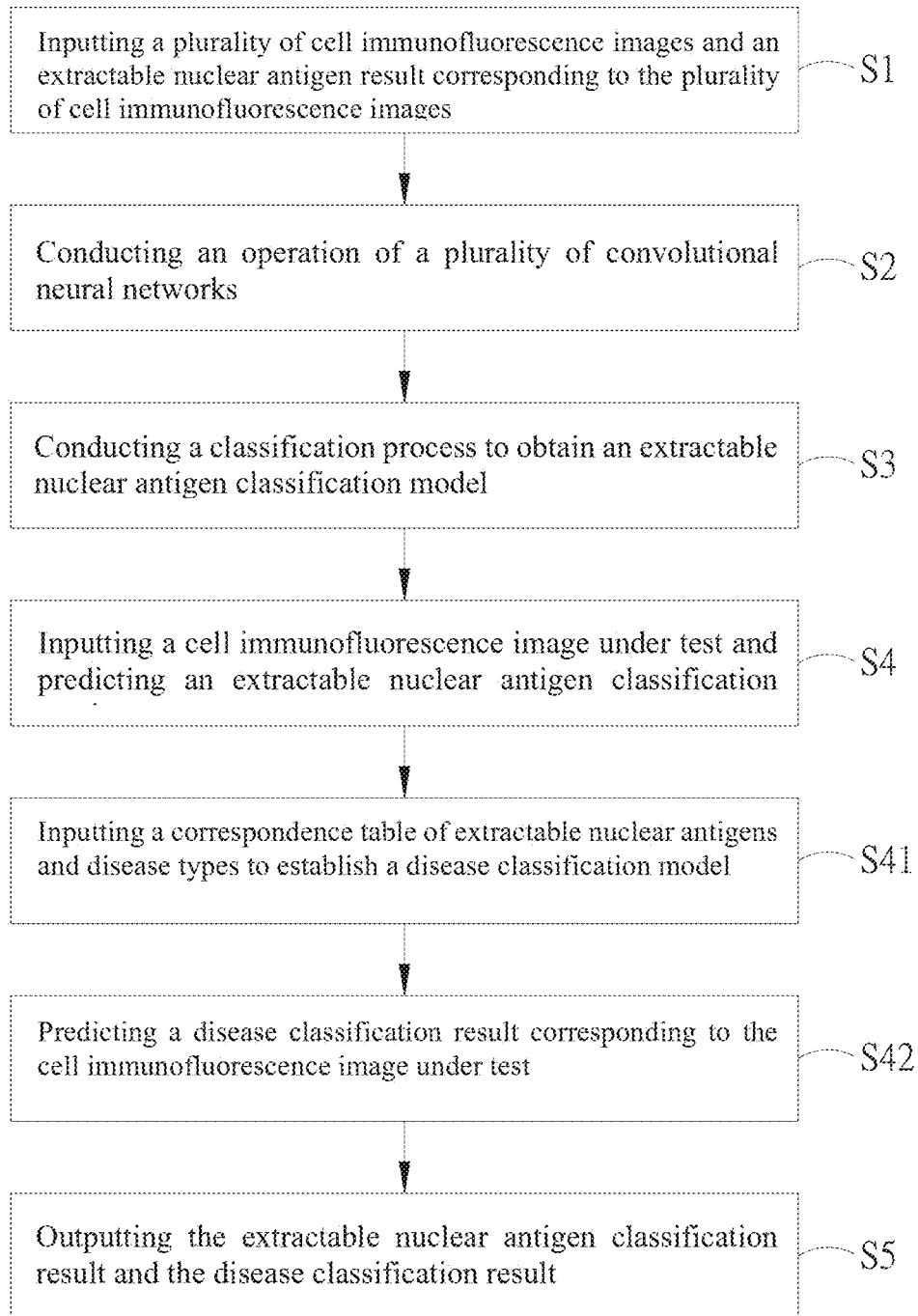
FIG. 4 is a flow chart showing a classification method of immunofluorescence images of autoantibodies according to another embodiment of the present invention.

Referring to FIG. 4, which is a flow chart showing a classification method of immunofluorescence images of autoantibodies according to another embodiment of the present invention. As shown in FIG. 4, the classification method of immunofluorescence images of autoantibodies comprises the same steps (S1 to S5) as the foregoing embodiment and additional steps (S41 to S42). In the present embodiment, the same steps as the foregoing embodiment are no longer repeatedly described, and only the difference portions are described as follows.

Step S41: Inputting a correspondence table of extractable nuclear antigens and disease types to establish a disease classification model. The examination type of extractable nuclear antigens can correspond to different disease types, which can be used as a recognition basis for classifying immune diseases. The correspondence table for the extractable nuclear antigens and the disease types is shown in Table 1, wherein each of the extractable nuclear antigens can correspond to more than one disease type.

TABLE 1

| No. | Extractable nuclear antigen type | Corresponding disease |
|---|---|---|
| 1 | dsDNA | Systemic lupus erythematosus (SLE) |
| 2 | ssDNA | Systemic lupus erythematosus (SLE) |
|   |   | Drug-induced SLE |
|   |   | Mixed connective tissue disease (MCTD) |

TABLE 1-continued

| No. | Extractable nuclear antigen type | Corresponding disease |
|---|---|---|
|   |   | Polymyositis |
|   |   | Dermatomyositis |
|   |   | Progressive systemic sclerosis (PSS) |
|   |   | Sjoren's syndrome (SjS) |
|   |   | Rheumatoid arthritis (RA) |
| 3 | RNA | Systemic lupus erythematosus (SLE) |
|   |   | Progressive systemic sclerosis (PSS) |
|   |   | Sjoren's syndrome (SjS) |
| 4 | Histone | Drug-induced SLE |
|   |   | Systemic lupus erythematosus (SLE) |
|   |   | Rheumatoid arthritis (RA) |
| 5 | U1-RNP | Mixed connective tissue disease (MCTD) |
|   |   | Systemic lupus erythematosus (SLE) |
|   |   | Rheumatoid arthritis (RA) |
| 6 | Sm | Systemic lupus erythematosus (SLE) |
| 7 | SS-A | Sjoren's syndrome (SjS) |
|   |   | Systemic lupus erythematosus (SLE) |
|   |   | Neonatal lupus syndrome |
| 8 | SS-B | Sjoren's syndrome (SjS) |
|   |   | Systemic lupus erythematosus (SLE) |
| 9 | U3-nRNP/Fibrillarin | Progressive systemic sclerosis (PSS) |
| 10 | RNA polymerase 1 | Progressive systemic sclerosis (PSS) |
| 11 | RNA helicase A | Systemic lupus erythematosus (SLE) |
| 12 | PM-Scl | Polymyositis |
|   |   | Dermatomyositis |
|   |   | Progressive systemic sclerosis (PSS) |
| 13 | centromeres (cenp-A, cenp-B) | Progressive systemic sclerosis (PSS) |
| 14 | Topoisomerase 1 | Progressive systemic sclerosis (PSS) |
| 15 | PCNA-like | Systemic lupus erythematosus (SLE) |
| 16 | Ku | Systemic lupus erythematosus (SLE) |
|   |   | Polymyositis |
|   |   | Dermatomyositis |
|   |   | Progressive systemic sclerosis (PSS) |
| 17 | Mi-1, Mi-2 | Dermatomyositis |
| 18 | Nucleosome | Systemic lupus erythematosus (SLE) |
| 19 | DFS-70 | Aopic dermatitis |
|   |   | Rheumatoid arthritis (RA) |
| 20 | TIF1-gamma | Dermatomyositis |
| 21 | hnRNP | Systemic lupus erythematosus (SLE) |
|   |   | Mixed connective tissue disease (MCTD) |
| 22 | RNA polymerase lll | Systemic lupus erythematosus (SLE) |
|   |   | Mixed connective tissue disease (MCTD) |
| 23 | Sp100 | Primary biliary cholangitis (PBC) |
| 24 | Sp140 | Primary biliary cholangitis (PBC) |
| 25 | p80-coilin | Sjoren's syndrome (SjS) |
|   |   | Systemic lupus erythematosus (SLE) |
| 26 | NOR-90 (nucelolus organisator) | Progressive systemic sclerosis (PSS) |
| 27 | gp210 | Primary biliary cholangitis (PBC) |
| 28 | lamin A, b, c and lamin B receptor | Primary biliary cholangitis (PBC) |
| 29 | F-actin | Autoimmune hepatitis (AIH) |
|   |   | Virus-indeuced hepatitis |
|   |   | Primary biliary cholangitis (PBC) |
| 30 | tropomyosin | Myasthenia gravis |
|   |   | Ulcerative colitis |
|   |   | Crohn's disease |
| 31 | vimentin | inflammatory reaction and infection |
| 32 | vinculin | Myasthenia gravis |
|   |   | Ulcerative colitis |
|   |   | Crohn's disease |
| 33 | GWB proteins (GW182) | Primary biliary cholangitis (PBC) |
|   |   | Neurological disease |
| 34 | PL-7, PL-12 | Myositis |
| 35 | ribosomal P | Systemic lupus erythematosus (SLE) |
| 36 | SRP | Polymyositis/Dermatomyositis |
|   |   | Necrotising myopathy |
| 37 | JO-1 | Polymyositis |
|   |   | Systemic lupus erythematosus (SLE) |
|   |   | Systemic sclerosis (SSc) |
|   |   | Interstitial lung disease |
|   |   | Raynaud's syndrome |
|   |   | Polysynovitis |
| 38 | AMA-M2 | Primary biliary cholangitis (PBC) |

TABLE 1-continued

| No. | Extractable nuclear antigen type | Corresponding disease |
|---|---|---|
| 39 | giantin/macrogolgin, golgin-95/GM130 | Systemic lupus erythematosus (SLE) Sjoren's syndrome (SjS) Rheumatoid arthritis (RA) |
| 40 | IMPDH2 (inosine monophosphate dehydrogenase 2) | Hepatitis C infections |
| 41 | pericentrin, ninein, Cep250 and Cep110 | Progressive systemic sclerosis (PSS) Raynaud's syndrome Infection |
| 42 | HsEG5(MSA-2) | Systemic lupus erythematosus (SLE) |
| 43 | NUMA(MSA-1) | Sjoren's syndrome (SjS) Anti-phospholipid syndrome (APS) Systemic lupus erythematosus (SLE) |
| 44 | CENP-F like | Cancer, other conditions |

Step S42: Predicting a disease classification result corresponding to the cell immunofluorescence image under test. Based on the correspondence table established above, the extractable nuclear antigen classification model established in the step S3 can be further extended to the disease classification model. That is, the cell immunofluorescence images are subjected to an operation of convolutional networks, linked to different extractable nuclear antigens, and further linked to different types of disease classification. After the input of the cell immunofluorescence image under test, the features calculated by the multi-layer operation of convolutional neural networks are linked to different types of disease classification, thereby predicting the classification result of the cell immunofluorescence image under test belonging to different disease types. The disease classification result may also be stored in the storage device, and transmitted to the corresponding processing personnel through an output device to assist the medical staff to recognize the cell immunofluorescence images belonging to the disease type, thereby improving the diagnostic efficiency.

Figure 5:
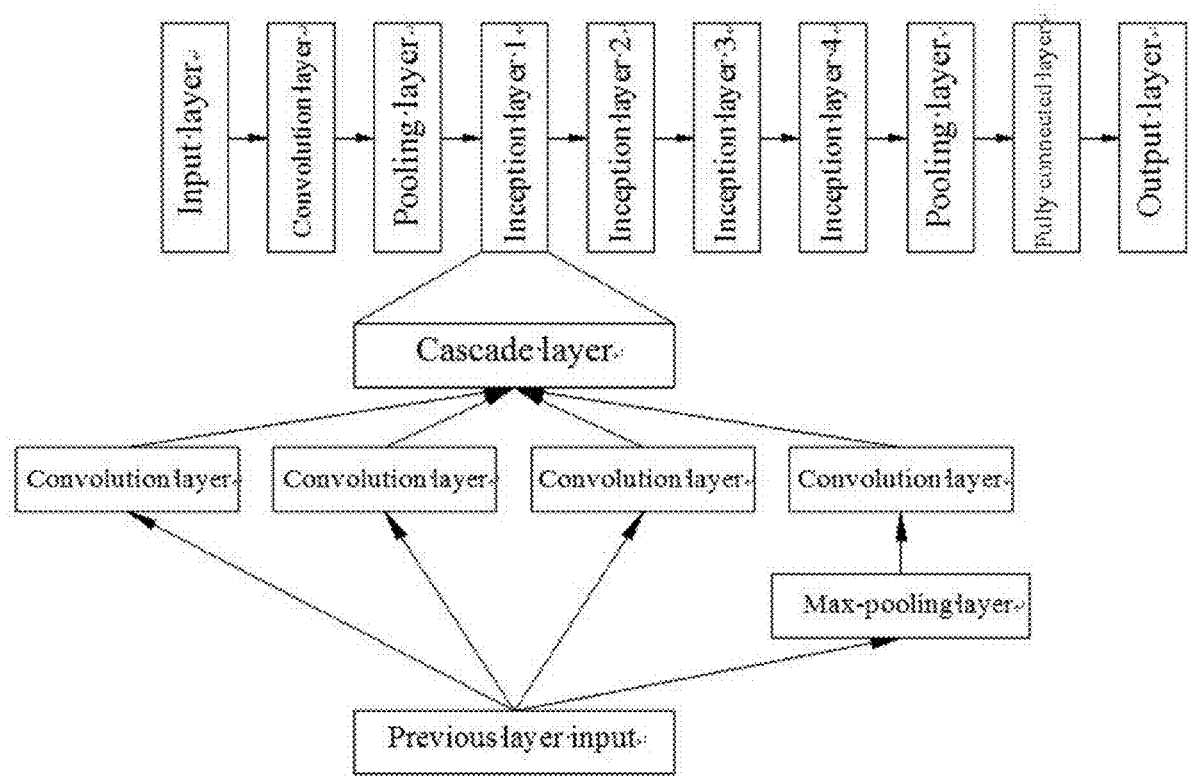
FIG. 5 is a schematic diagram showing a classification method of immunofluorescence images of autoantibodies according to an embodiment of the present invention.

Referring to FIG. 5, which is a schematic diagram showing a classification method of immunofluorescence images of autoantibodies according to an embodiment of the present invention. As shown in FIG. 5, in the present embodiment, a 10-layer convolutional neural network operation can be conducted corresponding to the above-described classification step. In detail, after inputting the cell immunofluorescence images from the input layer, the operations of the convolution layer and the pooling layer are conducted, followed by four times of the inception layer operation (inception layer 1 to inception layer 4), that is, after 16 times of convolutional neural network and finally through the pooling layer, a classification proportion linked to extractable nuclear antigens through the fully connected layer is generated, and finally it is outputted through the output layer. The operation of each of the inception layers can also be divided into multiple convolution layers and then integrated through the cascade layer. The detailed content thereof is similar to the inception layer operation of the foregoing embodiment, so the description is not repeated. Overall, the optimal results can be achieved in this embodiment through a 10-layer convolutional neural network operation. Among them, the convolution kernel size and data dimension design of each layer can be the same in each convolutional neural network operation block or can be adjusted according to requirements. At the same time, the more layers can be used to discover deeper features, but the corresponding operation time will increase, thus reducing the efficiency of analysis. Therefore, the number of convolutional neural network operations conducted in this embodiment and the number of operation layers of each block can be adjusted according to requirements.

Similar to the previous embodiment, in the portion of the output layer, the corresponding relationship between the extractable nuclear antigen and different disease types can be further combined, and the classification result of cell immunofluorescence images in different disease types is output. For example, the cell immunofluorescence images are recognized to include a negative, a nuclear, a cytoplasmic, and a mitotic phenotype via an operation of convolutional neural networks. Each phenotype can be further classified into the following feature patterns: a homogeneous pattern, a DFS pattern, a Centromere pattern, a Speckle pattern, a Nuclear dots pattern, a Nucleolar pattern, a Nuclear envelope pattern, a PCNA-like pattern, a CENP-F like pattern, a Fibrillar pattern, a GW body-like/lysosomal pattern, a Ribosomal pattern, a JO-1 like pattern, a mitochondrial pattern, a Golgi pattern, a Rods and rings pattern, a Centromere pattern, a Spindle fibers pattern, an MSA-1 pattern, and a centrophilin (NuMA) pattern. After the operation of the classification method of immunofluorescence images of autoantibodies in the present embodiment, the classification relationship as shown in Table 2 can be obtained, thereby establishing a disease classification model. According to this model, the cell immunofluorescence image under test is linked to different disease types, reducing the time required for manual interpretation of image types and blood examination for extractable nuclear antigens, and improving the accuracy of diagnosing disease types and the recognition efficiency of categorizing disease classifications.

TABLE 2

| Feature pattern | Extractable nuclear antigen type | Disease type |
|---|---|---|
| Homogeneous | dsDNA, nucleosomes, histones | SLE, Drug-induced SLE, juvenile idiopathic arthritis |
| DFS | DFS70/LEDGF | Sjoren's syndrome (SjS), SSc and SLE |
| Centromere | CENP-A/B (C) | SSc, PBC |
| Speckle | SS-A/Ro, SS-B/La, Mi-2, TIF1γ, TIF1β, Ku hnRNP, U1RNP, Sm, RNA polymerase III | SjS, SLE, Dermatomyositis MCTD, SLE, SSc |
| Nuclear dots | Sp-100, PML proteins, MJ/NXP-2 p80-coilin, SMN | PBC, SARD, Dermatomyositis SjS, SLE, SSc, PM, asymptomatic individuals |
| Nucleolar | PM/Scl-75, PM/Scl-100, Th/To, B23/ nucleophosmin, nucleolin, No55/SC65 | SSc, SSc/PM overlapping |
|  | U3-snoRNP/fibrillarin | SSc |
|  | RNA polymerase I, hUBF/NOR-90 (nucleolar organizer regions) | SSc, SjS |
| Nuclear envelope | lamins A, B, C, or lamin-associated proteins nuclear pore complex proteins (i.e. gp210) | SLE, SjS, seronegative arthritis PBC |
| PCNA-like | PCNA | SLE, other conditions |
| CENP-F like | CENP-F | Cancer, other conditions |
| Fibrillar | actin, non-muscle myosin | MCTD, chronic active hepatitis, liver cirrhosis, Myasthenia gravis, Crohn's disease, PBC, long term hemodialysis, rarely in SARD |

TABLE 2-continued

| Feature pattern | Extractable nuclear antigen type | Disease type |
|---|---|---|
| | vimentin, cytokeratins, tropomyosin | infectious or inflammatory conditions, long term hemodialysis, alcoholic liver disease, SARD, psoriasis, healthy controls |
| | alpha-actinin, vinculin | Myasthenia gravis, Crohn's disease, Ulcerative colitis |
| GW body-like/lysosomal | GW182, Su/Ago2 | PBC, SARD, neurological and autoimmune conditions |
| Ribosomal | PL-7, PL-12, ribosomal P proteins | anti-synthetase syndrome, PM/DM, SLE, juvenile SLE, neuropsychiatric SLE |
| JO-1 like | Jo-1/histidyl-tRNA synthetase | anti-synthetase syndrome, PM/DM, limited SSc, idiopathic pleural effusion |
| Mito-chondrial | PDC-E2/M2, BCOADC-E2, OGDC-E2, E1α subunit of PDC, E3BP/protein X | Generally in PBC, SSc, rarely in other SARD |
| Golgi | giantin/macrogolgin, golgin-95/GM130, golgin-160, golgin-97, golgin-245 | Rarely in SjS, SLE, RA, MCTD, GPA, idiopathic cerebellar ataxia, paraneoplastic cerebellar degeneration, viral infections |
| Rods and rings | IMPDH2 | HCV patient post-IFN/ ribavirin therapy, rarely in SLE, Hashimoto's and healthy controls |
| Centromere | pericentrin, ninein, Cep250, Cep110 | SjS, Raynaud's phenomenon, viral and mycoplasma |
| Spindle fibers | HsEg5 | SjS, SLE, other CTD |
| MSA-1, centrophilin (NuMA) | NuMA | SjS, SLE, others |

Figure 6:
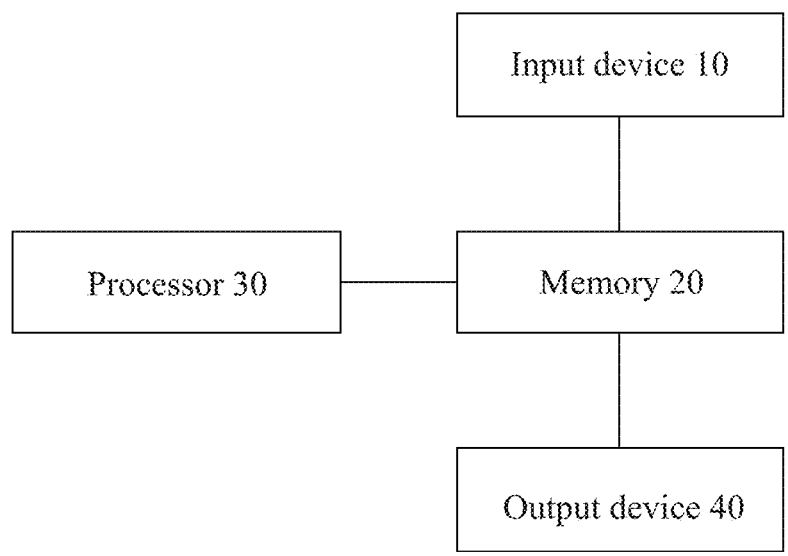
FIG. 6 is a block diagram showing a classification system of immunofluorescence images of autoantibodies according to an embodiment of the present invention.

The above mentioned classification method of immunofluorescence images of autoantibodies can be established in a specific system. Referring to FIG. 6, which is a block diagram showing a classification system of immunofluorescence images of autoantibodies according to an embodiment of the present invention. As shown in FIG. 6, the system comprises an input device 10, a memory 20, a processor 30, and an output device 40. The input device 10 herein comprises a shooting or capturing device, or an input interface (including a touch screen, a keyboard, a mouse, etc.) of an electronic device such as a personal computer, a smart phone, a server, etc., transmitting cell immunofluorescence images through a file. A plurality of cell immunofluorescence images and an extractable nuclear antigen result corresponding to the plurality of cell immunofluorescence images are input, and the data are uploaded to and stored in the memory 20 through wireless network transmission, wireless communication transmission or general limited internet. The memory 20 includes a read-only memory, a flash memory, a disk, or a cloud database.

In addition, the system further comprises a processor 30 connected to the memory 20, wherein the processor 30 comprises a central processing unit, an image processor, a microprocessor, etc., which may include a multi-core processing unit or a combination of multiple processing units. The processor 30 can access cell immunofluorescence images in the memory 20 for analysis, that is, through the classification method of the foregoing embodiment, a multi-layer convolution operation is conducted on the image, the extractable nuclear antigen result is fully connected according to the convolution features, and an extractable nuclear antigen classification model is established and stored in the memory 20. The extractable nuclear antigen classification model is trained and corrected according to the data of the confirmed extractable nuclear antigen result. When the cell immunofluorescence image under test is input through the input device 10, a plurality of extractable nuclear antigens corresponding to the cell immunofluorescence image under test are predicted according to the same convolution operation process and classification process. The predicted extractable nuclear antigen classification result is output through the output device 40, and the output method can also transmit the result to the computer, mobile phone or tablet of the medical staff or the medical examiner through wired or wireless network transmission, so that it can perform subsequent diagnosis or provide further instructions according to the classification result.

In addition, the input device 10 may further input a correspondence table of the extractable nuclear antigen corresponding to a plurality of disease types, and establish a disease classification model in which cell immunofluorescence images belong to different disease types through the processor 30. After the above setting, the cell immunofluorescence image under test predicts the disease type corresponding to the cell immunofluorescence image under test via the disease classification model, and the disease classification result thus generated is output through the output device 40 to provide a reference for the diagnosis of the medical staff.

Figure 7:
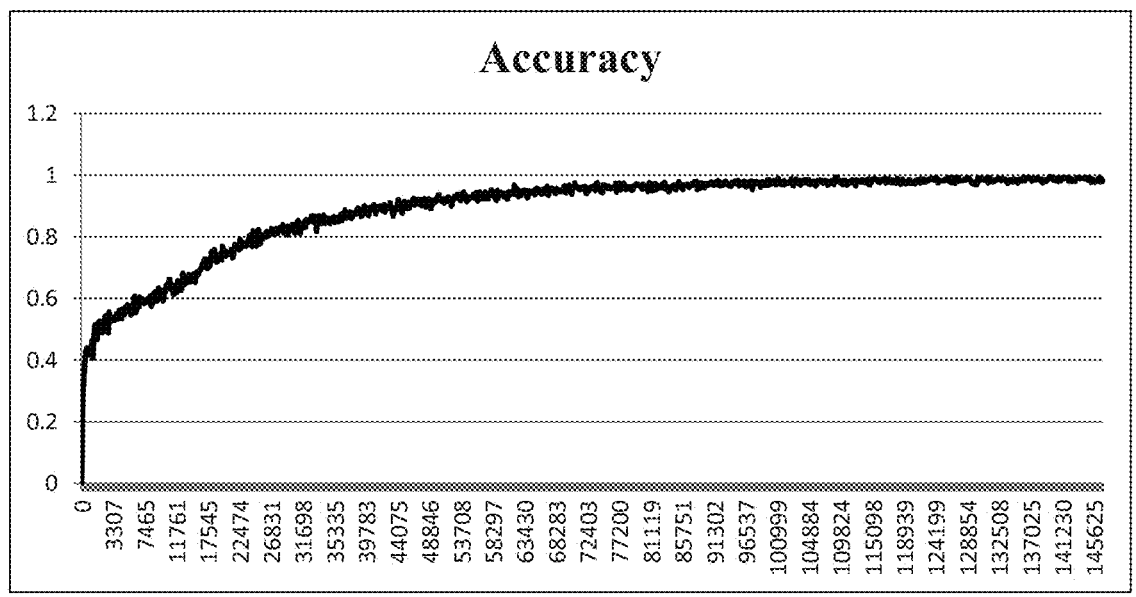
FIG. 7 is a schematic diagram showing the result of classification of an autoantibody according to an embodiment of the present invention.

In the following, the data of autoantibodies examined from the medical laboratory are analyzed. These data have been recognized by the clinician. The data on which the extractable nuclear antigen examination has been conducted can be selected as the input training data, so as to establish an extractable nuclear antigen classification model corresponding to immunofluorescence images of autoantibodies. The immunofluorescence images of autoantibodies under test are input, and after conducting a multi-layer operation of convolutional neural networks, the classification result is generated. Subsequently, compared with the actual detection result, the accuracy of the classification is examined Referring to FIG. 7, which is a schematic diagram showing the result of classification of an autoantibody according to an embodiment of the present invention. As shown in FIG. 7, the accuracy obtained in this embodiment can be 99.5034%, and it can be shown that regarding the accuracy of classification, the classification system and the classification method of immunofluorescence images of autoantibodies of the present embodiment can obtain good classification results.

Although the present invention has been described with reference to the preferred embodiments, it will be apparent to those skilled in the art that a variety of modifications and changes in form and detail may be made without departing from the scope of the present invention defined by the appended claims.

What is claimed is:

1. A classification system of immunofluorescence images of autoantibodies, comprising:
   a camera device configured to input a plurality of cell immunofluorescence images and an extractable nuclear antigen result corresponding to the plurality of cell immunofluorescence images;
   a processor connected to the camera device, wherein the processor converts the plurality of cell immunofluorescence images into a plurality of three primary color layers, respectively, and conducts an operation of a plurality of convolutional neural networks, wherein each of the plurality of convolutional neural networks comprises a convolution layer, a pooling layer and an inception layer for capturing a plurality of convolution features after the operation, wherein the plurality of convolution features are used as input of next order of the convolutional neural networks, wherein the plurality of convolution features are fully connected with the extractable nuclear antigen result, wherein the processor obtains an extractable nuclear antigen classification model through recognizing proportions of the plurality of cell immunofluorescence images and comparing the proportions of the plurality of cell immunofluorescence images to a plurality of extractable nuclear antigens; and an output device connected to the processor, wherein the output device outputs an extractable nuclear antigen classification result generated by the processor;

wherein the extractable nuclear antigen classification result is the plurality of extractable nuclear antigens predicted by the processor corresponding to a cell immunofluorescence image under test input by the camera device according to the extractable nuclear antigen classification model.

2. The classification system according to claim 1, wherein the camera device inputs a correspondence table of the plurality of extractable nuclear antigens corresponding to a plurality of disease types, the processor establishes a disease classification model by the plurality of cell immunofluorescence images belong to the plurality of disease types, and the output device outputs a disease classification result generated by the processor;

wherein the disease classification result is the plurality of disease types predicted by the processor corresponding to the cell immunofluorescence image under test according to the disease classification model.

3. The classification system according to claim 2, wherein the plurality of extractable nuclear antigens respectively correspond to at least one of the plurality of disease types.

4. The classification system according to claim 1, wherein the convolution layer comprises a trigger function, and the trigger function comprises a Sigmoid function, a Tanh function, a ReLU function, a PReLU function, an ArcTan function, an ELU function, a SoftPlus function, a Sinusoid function, a Sinc function, a Bent identity function, or a Gaussian function.

5. The classification system according to claim 1, wherein the pooling layer comprises a max-pooling operation or a mean pool operation.

6. The classification system according to claim 1, wherein the inception layer comprises a convolution operation and a max-pooling operation for different sizes of templates in a same layer of operation, and then data are cascaded.

7. The classification system according to claim 1, wherein each of the plurality of extractable nuclear antigens comprises at least one of a nucleic acid and a protein selected from the group consisting of: dsDNA, ssDNA, RNA, Histone, U14-RNP, Sm, SS-A, SS-B, U3-nRNP/Fibrillarin, RNA polymerase 1, RNA helicase A, PM-Scl, centromeres, Topoisomerase 1, PCNA-like, Ku, Mi-1, Mi-2, Nucleosome, DFS-70, TIF1-gamma, hnRNP, RNA polymerase III, Sp100, Sp140, p80-coilin, NOR-90, gp210, lamin A, b, c and lamin B receptor, F-actin, tropomyosin, vimentin, vinculin, GWB proteins, PL-7, PL-12, ribosomal P, SRP, JO-1, AMA-M2, giantin/macrogolgin, golgin-95/GM130, pericentrin, ninein, Cep250 and Cep110, HsEG5, NUMA, CENP-F like, and a combination thereof.

8. The classification system according to claim 1, wherein the plurality of cell immunofluorescence images is subjected to an operation of 10-layer convolutional neural networks to capture the plurality of convolution features.

9. The classification system according to claim 1, wherein the convolution layer in each of the plurality of convolutional neural networks has a convolution kernel of a predetermined pixel size.

10. A classification method of immunofluorescence images of autoantibodies, comprising the following steps:
inputting a plurality of cell immunofluorescence images and an extractable nuclear antigen result corresponding to the plurality of cell immunofluorescence images through a camera device;

converting the plurality of cell immunofluorescence images into a plurality of three primary color layers, respectively, and conducting an operation of a plurality of convolutional neural networks via a processor, wherein each of the plurality of convolutional neural networks comprises a convolution layer, a pooling layer and an inception layer for capturing a plurality of convolution features after the operation, followed by using the plurality of convolution features as input of next order of the convolutional neural networks;

conducting a classification process via the processor, fully connecting the plurality of convolution features with the extractable nuclear antigen result, and obtaining an extractable nuclear antigen classification model through recognizing proportions of the plurality of cell immunofluorescence images and comparing the proportions of the plurality of cell immunofluorescence images to a plurality of extractable nuclear antigens;

inputting a cell immunofluorescence image under test through the camera device, and predicting an extractable nuclear antigen classification result in the cell immunofluorescence image under test according to the extractable nuclear antigen classification model by the processor; and outputting the extractable nuclear antigen classification result through an output device.

11. The classification method according to claim 10, further comprising the following steps:
inputting a correspondence table of the plurality of extractable nuclear antigens corresponding to a plurality of disease types through the camera device, and establishing a disease classification model by the plurality of cell immunofluorescence images belong to the plurality of disease types through the processor;

predicting a disease classification result of the plurality of disease types corresponding to the cell immunofluorescence image under test according to the disease classification model via the processor; and outputting the disease classification result through the output device.

12. The classification method according to claim 11, wherein the plurality of extractable nuclear antigens respectively correspond to at least one of the plurality of disease types.

13. The classification method according to claim 10, wherein the convolution layer comprises a trigger function, and the trigger function comprises a Sigmoid function, a Tanh function, a ReLU function, a PReLU function, an ArcTan function, an ELU function, a SoftPlus function, a Sinusoid function, a Sinc function, a Bent identity function, or a Gaussian function.

14. The classification method according to claim 10, wherein the pooling layer comprises a max-pooling operation or a mean pool operation.

15. The classification method according to claim 10, wherein the inception layer comprises a convolution operation and a max-pooling operation for different sizes of templates in a same layer of operation, and then data are cascaded.

16. The classification method according to claim 10, wherein each of the plurality of extractable nuclear antigens comprises at least one of a nucleic acid and a protein selected from the group consisting of: dsDNA, ssDNA, RNA, Histone, U14-RNP, Sm, SS-A, SS-B, U3-nRNP/Fibrillarin, RNA polymerase 1, RNA helicase A, PM-Scl, centromeres, Topoisomerase 1, PCNA-like, Ku, Mi-1, Mi-2, Nucleosome, DFS-70, TIF1-gamma, hnRNP, RNA polymerase III, Sp100, Sp140, p80-coilin, NOR-90, gp210, lamin A, b, c and lamin B receptor, F-actin, tropomyosin, vimentin, vinculin, GWB proteins, PL-7, PL-12, ribosomal P, SRP, JO-1, AMA-M2, giantin/macrogolgin, golgin-95/GM130, pericentrin, ninein, Cep250 and Cep110, HsEG5, NUMA, CENP-F like, and a combination thereof.

17. The classification method according to claim 10, wherein the plurality of cell immunofluorescence images inputted are subjected to an operation of 10-layer convolutional neural networks to capture the plurality of convolution features.

18. The classification method according to claim 10, wherein the convolution layer in each of the plurality of convolutional neural networks has a convolution kernel of a predetermined pixel size.

* * * * *